United States Patent
Regensburger et al.

(10) Patent No.: US 11,950,949 B2
(45) Date of Patent: Apr. 9, 2024

(54) ANESTHESIA PROCEDURE AND ASSOCIATED EQUIPMENT

(71) Applicant: Siemens Healthcare GmbH, Erlangen (DE)

(72) Inventors: Alois Regensburger, Poxdorf (DE); Amilcar Alzaga, Bayern (DE)

(73) Assignee: Siemens Healthineers AG, Forchheim (DE)

( * ) Notice: Subject to any disclaimer, the term of this patent is extended or adjusted under 35 U.S.C. 154(b) by 218 days.

(21) Appl. No.: 17/312,641

(22) PCT Filed: Oct. 25, 2019

(86) PCT No.: PCT/EP2019/079120
§ 371 (c)(1),
(2) Date: Jun. 10, 2021

(87) PCT Pub. No.: WO2020/119993
PCT Pub. Date: Jun. 18, 2020

(65) Prior Publication Data
US 2022/0015733 A1  Jan. 20, 2022

(30) Foreign Application Priority Data

Dec. 14, 2018 (DE) .................... 10 2018 221 764.5
Apr. 18, 2019 (DE) .................... 10 2019 205 720.9

(51) Int. Cl.
A61B 6/00 (2006.01)
A61B 6/04 (2006.01)
(Continued)

(52) U.S. Cl.
CPC ............ *A61B 6/541* (2013.01); *A61B 6/0492* (2013.01); *A61B 6/488* (2013.01); *A61M 16/01* (2013.01);
(Continued)

(58) Field of Classification Search
CPC ....... A61B 6/541; A61B 6/0492; A61B 6/488; A61B 6/5294; A61B 5/064; A61M 16/01;
(Continued)

(56) References Cited

U.S. PATENT DOCUMENTS 6,597,939 B1 * 7/2003 Lampotang ............ A61B 6/541
128/202.16
7,393,329 B1 * 7/2008 Wong .................... A61M 16/00
600/428

(Continued)

FOREIGN PATENT DOCUMENTS

EP  0290062 A2  11/1988

OTHER PUBLICATIONS

Malinowski, Kathleen T., and Warren D. D'Souza. "Couch-based target alignment." Adaptive Motion Compensation in Radiotherapy. CRC Press, 2011. 57-64 (Year: 2011).*
(Continued)

*Primary Examiner* — Sean D Mattson
(74) *Attorney, Agent, or Firm* — Lempia Summerfield Katz LLC (57) ABSTRACT

The invention relates to an anaesthesia procedure and associated anaesthetic equipment (3). In said procedure, a first respiratory gas (G1) is supplied to an anaesthetized patient (15) through a ventilator (3) with unidirectional flow or rapidly alternating flow direction. At least one adjustment parameter (F) of the ventilator (3) is controlled or regulated
(Continued)

in such a manner that a current position (LA) of at least one body part (36) of the patient (15) is adjusted to a specified desired position (LS).

22 Claims, 5 Drawing Sheets (51) Int. Cl.
*A61M 16/01* (2006.01)
*A61B 5/06* (2006.01)
(52) U.S. Cl.
CPC ...... *A61B 5/064* (2013.01); *A61M 2205/3334* (2013.01)
(58) Field of Classification Search
CPC .......... A61M 2205/3334; G16H 20/40; G16H 30/40
See application file for complete search history.

(56) References Cited

U.S. PATENT DOCUMENTS

| 2007/0100233 | A1 | 5/2007 | Thomson | |
| 2008/0039713 | A1* | 2/2008 | Thomson | A61N 5/1039 382/294 |
| 2010/0222666 | A1 | 9/2010 | Foo | |
| 2013/0087145 | A1* | 4/2013 | Kobrich | A61M 16/203 128/203.14 |
| 2013/0116555 | A1* | 5/2013 | Kuzelka | A61M 16/024 600/1 |
| 2014/0066749 | A1* | 3/2014 | Dickerson | A61B 6/541 600/407 |
| 2016/0256710 | A1 | 9/2016 | Goldstein et al. | |
| 2017/0135599 | A1* | 5/2017 | Brown | A61M 16/021 |
| 2018/0236193 | A1* | 8/2018 | Parkes | A61N 5/1048 |

OTHER PUBLICATIONS

Fleming, Susannah, et al. "Normal ranges of heart rate and respiratory rate in children from birth to 18 years of age: a systematic review of observational studies." The Lancet 377.9770 (2011): 1011-1018. (Year: 2011).*
Hooker, Edmond A., et al. "Respiratory rates in emergency department patients." The Journal of emergency medicine 7.2 (1989): 129-132. (Year: 1989).*
Fischer, Peter, Thomas Pohl, and Joachim Hornegger. "Real-time respiratory signal extraction from x-ray sequences using incremental manifold learning." 2014 IEEE 11th International Symposium on Biomedical Imaging (ISBI). IEEE, 2014. pp. 915-918.
German Office Action for German Application No. 10 2018 221 764.5 dated Sep. 30, 2019.
International Search Report and the Written Opinion for International Patent Application PCT/EP2019/079120 dated Feb. 18, 2020.
Malinowski Kathleen T. et al.: "Couch-Based Target Alignment"; Adaptive Motion Compensation in Radiotherapy, CRC Press LLC, pp. 39-46; 2011.
Patel, A., and SA Reza Nouraei. "Transnasal Humidified Rapid-Insufflation Ventilatory Exchange (THRIVE): a physiological method of increasing apnoea time in patients with difficult airways." Anaesthesia 70.3 (2015): 323-329.
Wikipedia: "Components of a typical machine", 2018, https://en.wikipedia.org/wiki/Anaesthetic_machine; pp. 1-1 excerpt.
Yoganathan, S. A., et al. "Magnitude, impact, and management of respiration-induced target motion in radiotherapy treatment: a comprehensive review." Journal of medical physics 42.3 (2017): 101. pp. 1-31.

* cited by examiner

ANESTHESIA PROCEDURE AND ASSOCIATED EQUIPMENT

CROSS REFERENCE TO RELATED APPLICATIONS

This present patent document is a § 371 nationalization of PCT Application Serial No. PCT/EP2019/079120 filed on Oct. 25, 2019, designating the United States, which is hereby incorporated in its entirety by reference. This patent document also claims the benefit of DE 102018221764.5 filed on Dec. 14, 2018 and DE 102019205720.9 filed on Apr. 18, 2019 both of which are hereby incorporated in their entirety by reference.

FIELD

Embodiments relate to an anesthesia procedure and associated equipment.

BACKGROUND

Respiratory movements displace the organs and other body parts (for example abdominal wall, diaphragm, etc.) in the abdominal region of a patient. The movement leads to complicated conditions in the case of medical imaging methods as well as image-guided medical examinations and treatments. For example, the respiration-induced movement of organs and other body parts complicates the guidance of a needle or a catheter in the case of a minimally invasive medical procedure since, owing to the movement of the abdominal region, at most instants the current location of the organs and other body parts does not match the location that emerges from a planning scan (in other words, a medical image data set acquired for treatment planning).

Image-guided medical treatments, in which what is known as a "2D/3D overlay" or an "augmented reality" representation are used, also become complicated. In the former case, high-resolution image data of the inside of the body of the patient, that was acquired before the treatment (for example computed tomography data), is overlaid with a moved live image, acquired during the treatment, having a lower degree of detail, a different dimensionality, or a different information content (for example, a fluoroscopy image). In the latter case, graphical or alphanumerical additional information is overlaid on the live images acquired during the treatment, for example tissue-specific colorings, lines for graphical emphasis of organ boundaries, etc.). In both cases the respiration-induced body movement leads to the overlays regularly not matching the information of the live images.

In the case of imaging medical methods, whose acquisition time lies in the order of magnitude of one or more respiratory cycles, for example computed tomography (CT), Dyna-CT or magnetic resonance tomography (MR), the respiration-induced body movement regularly leads to a loss in quality or to artefacts since the organs and other body parts move during the acquisition time.

In order to avoid the problems, until now the respiratory movement of the patient has been temporarily suppressed during a medical image acquisition or treatment of the type mentioned above. In the simplest case this may be achieved by requesting the patient to actively hold their breath during the image acquisition or treatment. This is only possible with cooperative, awake and physically suitable patients, however. In addition, active breath holding frequently leads to only partial suspension of the body movement. Often a shaking movement caused by the suppressed respiratory reflex takes the place of the normal respiratory movement, and this runs contrary to the desired reduction in movement.

Alternatively, in the case of anesthetized patients sometimes the respiratory movement is temporarily deactivated by stopping the artificial ventilation. This is only possible for a short time, however, without risking an undersupply of oxygen to the patient. In addition, a particular body state (and therewith a particular organ location) may be set only with a high level of inaccuracy by stopping the artificial ventilation. As a rule, the resting state established by switching off the artificial ventilation differs to a greater or lesser extent from the desired body state, therefore.

A further possibility for reducing the respiratory movement in the case of anesthetized patients is what is known as jet ventilation. Here, the respiratory gas is applied in a pulsed manner at a high pressure and with a high pulse frequency—compared to the duration of a customary respiratory cycle—through thin lines into the airways that are open to the outside. As a result of jet ventilation, the customary respiratory movement is replaced by a movement with significantly higher frequency and lower amplitude, that only slightly affects the location of organs and other body parts in the abdominal region and chest area.

Finally, a motionless ventilation technique is known by the name of THRIVE (Transnasal Humidified Rapid-Insufflation Ventilatory Exchange). In this case, the patient is supplied continuously and in an unmodulated manner, conventionally through the nose, with an oxygen-rich respiratory gas (for example pure oxygen) at a high flow rate of, for example, 70 liters per minute while the patient is anaesthetized. The high flow of oxygen at the nose ensures that the patient's blood is sufficiently supplied with oxygen over a period of up to approximately half an hour.

Conventionally, no pre-determined body state is achieved even with the use of jet ventilation or THRIVE ventilation. The problems illustrated above are only partially solved even with jet ventilation or THRIVE, therefore.

BRIEF SUMMARY AND DESCRIPTION

The scope of the embodiments is defined solely by the appended claims and is not affected to any degree by the statements within this summary. The present embodiments may obviate one or more of the drawbacks or limitations in the related art.

Embodiments provide an improved anesthesia procedure and associated equipment for a variably adjustable body state for a period of time in the case of an anesthetized patient.

In a first step, a (human or animal) patient is anesthetized (hereinafter anesthesia for short) in which the patient's own respiratory drive (spontaneous respiration) is suspended. This first step may be configured as part of the anesthesia procedure, for example when it is carried out automatically by anesthesia equipment. It may take place in advance of the actual anesthesia procedure but may also be a step triggered thereby, for example by the anesthesia being initiated by an anesthetist independently of the anesthesia equipment. The anesthetized state is, for example, a general anesthesia in which the consciousness and pain perception of the patient is deactivated in a manner that is customary per se.

During the anesthesia a first respiratory gas is supplied to the patient during the course of the anesthesia procedure by a ventilator, with a unidirectional flow or rapidly alternating flow direction.

THRIVE or jet ventilation may be used in order to supply the first respiratory gas with unidirectional flow.

When THRIVE is used the first respiratory gas is supplied continuously and in an unmodulated manner at a high flow rate. The supplied gas escapes via the airways that are open to the outside of the patient. A high flow rate in this case designates a flow rate that is customary in THRIVE anesthesia, that is, for example, at least 30 liters per minute and for example, 70 liters per minute. Pure oxygen or a gas mixture with, for example, at least 70% by volume oxygen may be used as the first respiratory gas.

When jet ventilation is used the first respiratory gas is likewise supplied unidirectionally, but modulated in a pulsed or impulsive manner, with the supplied gas again escaping through the airways that are open to the outside of the patient. The frequency of the pulses with which the first respiratory gas is supplied is significantly higher than the frequency of the customary respiratory cycle. For example, the first respiratory gas is supplied at a pulse frequency of approx. 0.5 to 10 Hertz. Air with a customary or slightly enriched oxygen content may be used as a first respiratory gas in this case.

Alternatively, a ventilation method is used in which the flow direction of the first respiratory gas is actively alternated by the ventilator with a frequency that significantly exceeds the frequency of the customary respiratory cycle.

In all cases the first respiratory gas optionally also contains a gaseous anesthetic, for example laughing gas (nitrous oxide, $N_2O$) or a mixture of gaseous anesthetics. In addition, or alternatively, the first respiratory gas may be humidified and/or temperature-controlled.

Since the first respiratory gas is supplied with unidirectional flow or rapidly alternating flow direction, the supply of the first respiratory gas is not connected with the movement of the patient's body, that would be comparable with the customary respiratory movement. At most, the organs and other body parts in the abdominal region and chest area of the patient are subject, for example when jet ventilation is used, to a significantly faster movement with much lower amplitude. The supply of the first respiratory gas described above will hereinafter be referred to as "motionless ventilation", therefore irrespective of the method variant specifically used.

With the motionless ventilation at least one adjustment parameter of the ventilator is controlled or regulated in such a way that a current location of at least one body part of the patient is adjusted to a specified desired location. The body part is, for example, an organ (for example kidneys, stomach, heart, lungs, etc.) arranged in the abdominal region or chest area of the patient or a different body part (for example abdominal wall, diaphragm, thorax, etc.). During the course of the adjustment the current location of the body part is approached, for example as far as possible, to the desired location or coincides with the desired location within specified tolerance limits.

In an embodiment, the adjustment parameter of the ventilator may be controlled or regulated in such a way that the specified desired location is adjusted to a specified temporal desired path. The specified desired path may include, for example, a temporal sequence of a plurality of desired locations. For example, intermittently stationary adjustment of the desired location to the specified desired path may occur due to the control or regulation of the ventilator here. The course over time of a movement of the current location of the at least one body part of the patient may be controlled or regulated hereby.

In an embodiment, the desired location may be specified on the basis of a schedule of a device for irradiation. The controlled or regulated approach of the current location to the desired location may hereby take place as part of the schedule. The schedule may include a temporal sequence of a plurality of operating parameters of the ventilator and/or further medical equipment. Furthermore, the schedule may include the output of an instruction to an operator, for example for adjustment of an operating parameter. The schedule may also include a temporal sequence of a plurality of specified desired locations. For example, a movement of the at least one body part of the patient along a desired path specified by the schedule may be specified hereby. Furthermore, the schedule may specify at least one location and/or a region, that, within a predetermined period of time, are excluded from the specification as a desired location. This may make it possible, for example, to avoid particular desired locations as part of the schedule.

In an embodiment, the device for irradiation is movable. A regulated adjustment of the desired location and a movement trajectory of the device for irradiation may take place. A regulated adjustment of the desired location to a movement trajectory, for example a specified one, of the device for irradiation may take place. Furthermore, a regulated adjustment of the movement trajectory of the device for irradiation to the desired location may be provided. A synchronized movement of the device for irradiation relative to the specified desired location may take place hereby.

For example, the regulated adjustment of the desired location may provide a specification of the desired location, synchronized with the movement of the device for irradiation, inside or outside of a target area of the device for irradiation. Targeted positioning of the at least one body part inside or outside of a target area of the device for radiation may be achieved hereby.

In an embodiment, a control parameter of the device for irradiation may be adjusted as a function of the current location. For example, a clocked adjustment of the control parameter of the device for irradiation may be provided as a function of the current location. Furthermore, a dynamic adjustment of the control parameter may be provided as a function of the current location. The control parameter may be used, for example, to control a movement of a movable device for irradiation and/or irradiation intensity.

In an embodiment, the patient is arranged on a movable patient supporting device. The current location of the at least one body part of the patient may be adjusted to the specified desired location at least partially by the movement of the patient supporting device. A number of degrees of freedom of movement of the at least one body part of the patient on adjustment to the desired location may be expanded by the degrees of freedom of the movable patient supporting device. Synchronized control of the movement of the patient supporting device and the adjustment of the current location to the desired location may take place by the ventilator. The adjustment of the current location to the specified desired location at least partially by the movement of the patient supporting device may provide a physically larger range of movement of the at least one body part of the patient. Furthermore, adjustment or orientation and/or a location of the at least one body part may take place due to the movement of the patient supporting device. In addition, a positioning and orientation of at least one further body part of the patient inside and/or outside of a specified spatial region may be provided by, for example regulated, adjustment of the current location to the desired location by the ventilator and by a corresponding movement of the patient supporting device. The at least one adjustment parameter of the ventilator is, for example, a flow rate, a pressure (for example averaged over time) or an oxygen concentration of the first respiratory gas. If the first respiratory gas is modulated, for example supplied with periodically varying or alternating pressure or periodically varying or alternating flow rate, the controlled or regulated adjustment parameter may be the modulation of the first respiratory gas, for example the frequency, amplitude and/or pulse form with which the flow rate or the pressure of the first respiratory gas vary or alternate. An individual adjustment parameter of the ventilator or any combination of adjustment parameters (for example any combination of the adjustment parameters mentioned above) may be varied during the course of the described control or regulation. The oxygen concentration of the first respiratory gas is regulated as a function of the through-flow rate in order to keep the oxygen consumption low—while ensuring an adequate oxygen supply to the patient. For example, the first respiratory gas is set at a through-flow rate of 70 liters/minute at 95% oxygen content, and at a through-flow rate of 60 liters/minute at 100% oxygen content.

Embodiments are based on the recognition that the location of organs and other body parts in the abdominal region and chest area of the patient is influenced by a variation of one or more adjustment parameter(s) of a ventilator for motionless ventilation of the patient in a manner similar to customary respiratory activity since the gas volume in the lungs of the patient may be varied by the respective adjustment parameter. As is known, owing to the motionless ventilation but—unlike with customary respiratory activity—particular body states may be kept constant, or may be maintained with only a slight fluctuation, over time. The location of organs and other body parts in the abdominal region and chest area of the patient may be adjusted precisely and—at least for a certain period of time—without the risk of an undersupply of oxygen to the patient, due to a variation in the at least one adjustment parameter of the ventilator.

In an embodiment of the procedure, the desired location of the body part is determined on the basis of an image data set of the inside of the body of the patient acquired by a medical imaging device. This image data set (hereinafter referred to as a "default image data set") is acquired, for example (but not imperatively), before the anesthesia. The imaging device is, for example, a radiography device, fluoroscopy device, a computed tomography device (CT), an angiography device or a Dyna-CT device, a magnetic resonance tomography device (MRT) or a 3D ultrasound device.

If the desired location of the body part, as described above, is determined from a default image data set, a closed-loop control may be carried out for the adjustment of the current location of the body part to the specified desired location. A current image data set (for example by radiography, fluoroscopy or 2D ultrasound) of the inside of the body of the patient is acquired during the anesthesia. The current location of the body part is determined from this current image data set. On the basis of a comparison of the current location with the desired location the at least one adjustment parameter of the ventilator is changed in such a way that the current location of the body part approaches the desired location. This closed-loop control may be carried out iteratively (in other words, repeated multiple times), so the current location of the body part is successively adjusted to the desired location. This iterative process may be carried out until a termination criterion is met (for example maximum approach of the current location to the desired location or approach of the current location to the desired location within a specified tolerance limit).

In an alternative embodiment, the desired location of the body part is determined indirectly on the basis of a desired position of at least one marking provided in or on the patient. The location of the body part to be adjusted is inferred from the position of the marking(s).

In an embodiment of the closed-loop control for adjustment of the current location of the body part to the specified desired location, a current position of the at least one marking is determined. The at least one adjustment parameter of the ventilator is changed in such a way that the current location of the at least one marking approaches an associated desired position of this marking. The closed-loop control may also be carried out iteratively with successive approach of the current position of the at least one marking to its desired position and, for example, until a specified termination criterion is met.

The at least one marking (fiducial marker) is, for example, an adhesive marking applied to the skin of the patient or a magnetic sensor arranged on or in the patient. The position of the marking or markings in the three-dimensional space is detected, for example, by a suitable tracking system, for example a (3D) camera or a magnetic tracking system here.

The two variants described above for determination of the current location of the body part and the envisaged desired location, namely the direct location determination from an image data set of the inside of the body and indirect location determination by the tracking of markings provided on or in the patient body may also be used in combination with each other, for example in that the current location and/or the desired location are determined by averaging the results of the two location determination methods.

A combination of image-assisted and marking-assisted location determination may also be used for the closed-loop control for adjustment of the current location of the body part to the desired location.

In an embodiment, the required direction and strength of the adjustment of the at least one adjustment parameter of the ventilator is derived in a learning-based manner by observation of the customary respiratory cycle. The typical image changes during a respiratory cycle are learned, for example, from an acquired sequence of fluoroscopy data. An optimized change in the at least one adjustment parameter of the ventilator is then determined on the basis of the learned knowledge. The direction in which and/or how strongly the at least one adjustment parameter of the ventilator has to be changed is derived from the acquired respiratory cycle, for example automatically, in order to establish the desired location of the body part. In addition, or alternatively, with indirect determination of the desired location by way of the desired position of the at least one marking, the movement of the marking during a respiratory cycle is recorded to derive an optimized adjustment of the at least one adjustment parameter of the ventilator.

In an embodiment, a subsequent image acquisition of the inside of the body of the patient or an intervention inside the body of the patient (for example a minimally invasive diagnostic or surgical measure, such as guidance of a needle or catheter) is triggered by the adjustment of the current location of the body part to the desired location. The image acquisition or intervention may be started or provided (and for example automatically) when (as soon as) the adjustment of the current location of the body part to the desired location is completed.

The image acquisition or intervention is provided, for example, by generation of a (for example optical, acoustic or electrical) provide signal or by automatic release of a corresponding medical device that performs the image acquisition or intervention. Because the image acquisition or intervention are triggered by the anesthesia procedure, it is possible to make efficient utilization of the period of time during that the patient may be ventilated without risk and without conventional (motion) respiratory movement. From experience this period of time is limited in that the $CO_2$ content in the blood gradually increases in the case of motionless ventilation (for example by THRIVE).

In an embodiment, at the end of or during an interruption to the image acquisition or intervention, a shift is made, for example automatically, from the motionless ventilation technique with unidirectional or rapidly alternating gas flow to a motion ventilation technique in which the patient is ventilated with a second respiratory gas with slowly alternating flow direction. The ventilation technique typically carried out by a conventional anesthetic apparatus, in which a respiratory gas is supplied to a patient with a frequency corresponding substantially to the customary respiratory cycle (comparatively slow, therefore) and a volume of gas corresponding to the customary respiratory activity, and in which the supplied respiratory gas is also actively removed again is referred to as "motion ventilation". The respiratory gas (hereinafter also referred to as the second respiratory gas) used for the motion ventilation is, for example, air with a customary or slightly enriched oxygen content and optionally at least one gaseous anesthetic. The second respiratory gas may also be humidified and/or temperature-controlled. For example, the flow direction of the respiratory gas during motion ventilation is alternated with a frequency between approx. 0.1 Hz and 0.5 Hz. Compared to the first respiratory gas used in the case of THRIVE anesthesia, the second respiratory gas is, for example, comparatively low in oxygen.

The anesthesia equipment is, in general, configured for automatic implementation of the anesthesia procedure described above, wherein the anesthesia equipment optionally interacts with medical imaging equipment and/or a tracking system.

The above-described embodiments of the anesthesia procedure find their equivalence in associated embodiments of the anesthesia equipment, therefore. The effects and advantages described in connection with the anesthesia procedure may be transferred to the corresponding embodiments of the anesthesia equipment, and vice versa, therefore.

Specifically, the anesthesia equipment includes a ventilator, that in a first operating mode ("motionless ventilation") is configured to supply a patient with a first respiratory gas (as described above) with unidirectional flow (for example unmodulated analogous to THRIVE or modulated analogous to jet ventilation) or with rapidly alternating flow direction. The anesthesia equipment also includes a control unit, that, as described above, is configured to control or regulate at least one adjustment parameter of the ventilator in order to adjust a current location of at least one body part of the patient to a specified desired location.

The control unit (controller) is optionally formed as a programmable component (for example as a processor, microcontroller, or personal computer) or as a non-programmable electronic circuit (for example in the form of an ASIC) or by a combination of programmable and non-programmable components. In the first case, the equipment of the control unit for carrying out the anesthesia procedure includes a control program (in other words, software), that is implemented to be executable in the control unit, and when run carries out the respective functions automatically or partially automatically in interaction with a user. In the second case, the functionality described above and below is implemented in terms of hardware in the control unit.

In an embodiment, the control unit is configured to control or regulate at least one adjustment parameter of the ventilator for adjustment of the specified desired location to a specified temporal desired path.

In an embodiment, the control unit is configured to specify the desired location on the basis of a schedule of a device for irradiation. The schedule may include a temporal sequence of a plurality of operating parameters of the ventilator and/or further medical devices. The operating parameters may include, for example, a spatial distribution of an irradiation dose for irradiation of the at least one body part of the patient. Specification of the desired location as a function of the schedule may provide safe and regulated irradiation of the at least one body part of the patient by the device for irradiation, therefore. Furthermore, specification of the desired location as a function of the schedule may ensure, for example, adherence to a specified spatial distribution of the irradiation dose.

In an embodiment, the control unit is configured to perform a regulated adjustment of the desired path and a movement trajectory of the device for irradiation on irradiation of the at least one body part of the patient by a movable device for irradiation. For example, a synchronized adjustment of the desired path and movement of the device for irradiation may take place hereby. This embodiment may be advantageous, for example, with targeted irradiation of the at least one body part. The synchronized adjustment of the desired path to the movement trajectory of the device for irradiation may also provide positioning of further body parts of the patient outside of a target area of the device for irradiation.

In an embodiment, the control unit is configured to adjust a control parameter of the device for irradiation, for example during an irradiation of the at least one body part of the patient, as a function of the current location. If the control parameter includes information on control of an irradiation intensity of the device for irradiation, for example a clocked or dynamically adjusted irradiation of the at least one body part of the patient may take place. Here the irradiation may be interrupted, for example with an inadequate adjustment of the current location to the specified desired location. Furthermore, the irradiation may be interrupted, for example with an identification of a further body part of the patient within the target area of the device for irradiation.

Furthermore, the adjustment of the control parameter may provide adherence to a specified spatial distribution of an irradiation dose of the at least one body part of the patient. For example, with an adjustment of the desired location to a specified desired path, guided and safe irradiation of the at least one body part at different specified desired locations may take place with an irradiation intensity pre-determined in each case. If a desired location along the desired path is specified several times, a division of the radiation dose applied in each case into a plurality of applications separated over time may be advantageous.

In an embodiment, the control unit is configured to adjust the current location of the at least one body part of the patient, that is arranged on a movable patient supporting device, to the specified desired location at least partially by a movement of the patient supporting device. This may provide, for example with an irradiation of the at least one body part of the patient by a device for irradiation, that a specified spatial distribution of the irradiation dose is adhered to inside and outside of the target area of the device for irradiation.

In an embodiment, the control unit is configured to determine the desired location of the body part on the basis of a default image data set of the inside of the body of the patient acquired by a medical imaging device (for example as described above). In addition, or alternatively, the control unit is configured to determine the desired location of the body part indirectly on the basis of a desired position of at least one marking provided in or on the patient (for example as described above) detected by a tracking unit.

For adjustment of the current location of the body part to the desired location determined in this way (indirectly or directly), the control unit carries out one of the closed-loop controls described in connection with the anesthesia procedure.

In an embodiment, the control unit is also configured to start or provide image acquisition of the inside of the body of the patient or an intervention in the inside of the body of the patient (for example as described above) after adjustment of the current location of the body part to the desired location.

In an embodiment of the anesthesia equipment, in a second operating mode ("motion ventilation") the ventilator is configured to supply the patient with a second respiratory gas with slowly alternating flow direction. Reference is again made to the preceding statements relating to the anesthesia procedure with regard to the make-up of the second respiratory gas and the typical frequencies of the alternation of the flow direction.

In an embodiment, the control device is configured to (for example, automatically) switch over the ventilator from the first operating mode into the second operating mode at the end of or during an interruption to the image acquisition or the intervention.

The ventilator, that may be operated in the two described operating modes, is a single, combined ventilator. Alternatively, the ventilator may also be formed by two separate pieces of apparatus for motionless ventilation or motion ventilation, for example by a THRIVE machine that is conventional per se and an anesthetic apparatus that is conventional per se, between which it is possible to switch by a shared controller. In an embodiment, the two partial pieces of apparatus of the ventilator are connected to each other by a ventilation tube branched in the shape of a Y, so the two partial pieces of apparatus output the respective respiratory gas into the same ventilation tube. The shared controller is in this case formed, for example, by a switchover valve with which, alternately, one of the two partial pieces of apparatus in each case may be connected to the shared strand of the ventilation tube.

The ventilator, that may be switched between motionless ventilation and motion ventilation, provides a fast and simple alternation between these two forms of ventilation. This in turn makes it possible to make good use of the period available to the patient for motionless ventilation without risk, for example in order to carry out image acquisitions or interventions, that would be hindered by a respiration-induced body movement.

The ventilator, that may be switched between the two operating modes as described above, namely motionless ventilation and conventional motion ventilation, may be an independent embodiment, that may also be used independently of the further features of the above-described anesthesia procedure and the associated equipment.

An embodiment includes in the use of a ventilator, that is configured to supply a patient with a first respiratory gas with unidirectional flow (for example unmodulated analogous to THRIVE or modulated analogous to jet ventilation) or with rapidly alternating flow direction in order to adjust a current location of at least one body part of the patient to a specified desired location.

An embodiment is a computer program product with a computer program, that may be loaded directly into a storage device of a computer and that contains program segments for activation of a ventilator for motionless ventilation of a patient (in other words for ventilation with unidirectional flow or rapidly alternating flow direction of a first respiratory gas). The program segments, when the computer program is run in the computer, control or regulate an adjustment parameter of the ventilator in such a way that a current location of at least one body part of the patient is adjusted to a specified desired location. In an expedient embodiment, the computer program product is formed by a computer-readable medium, for example a CD-ROM, DVD, a flash memory (for example as a USB stick or SD card) or a hard drive on which the computer program is stored.

The term "first respiratory gas" serves merely for conceptual differentiation from the "second respiratory gas" optionally used for motion ventilation. This choice of term does not imply that a second respiratory gas would necessarily be used. Similarly, the term "first operating mode" does not assume the necessary existence of the "second operating mode".

Furthermore, the terms "first respiratory gas" and "second respiratory gas" identify only the different application situation of these respiratory gases with motionless or motion ventilation. These two respiratory gases are, as a rule, also chemically different. They may alternatively also be chemically identical, however, and, for example, be taken from the same gas reservoir.

DETAILED DESCRIPTION

Figure 1:
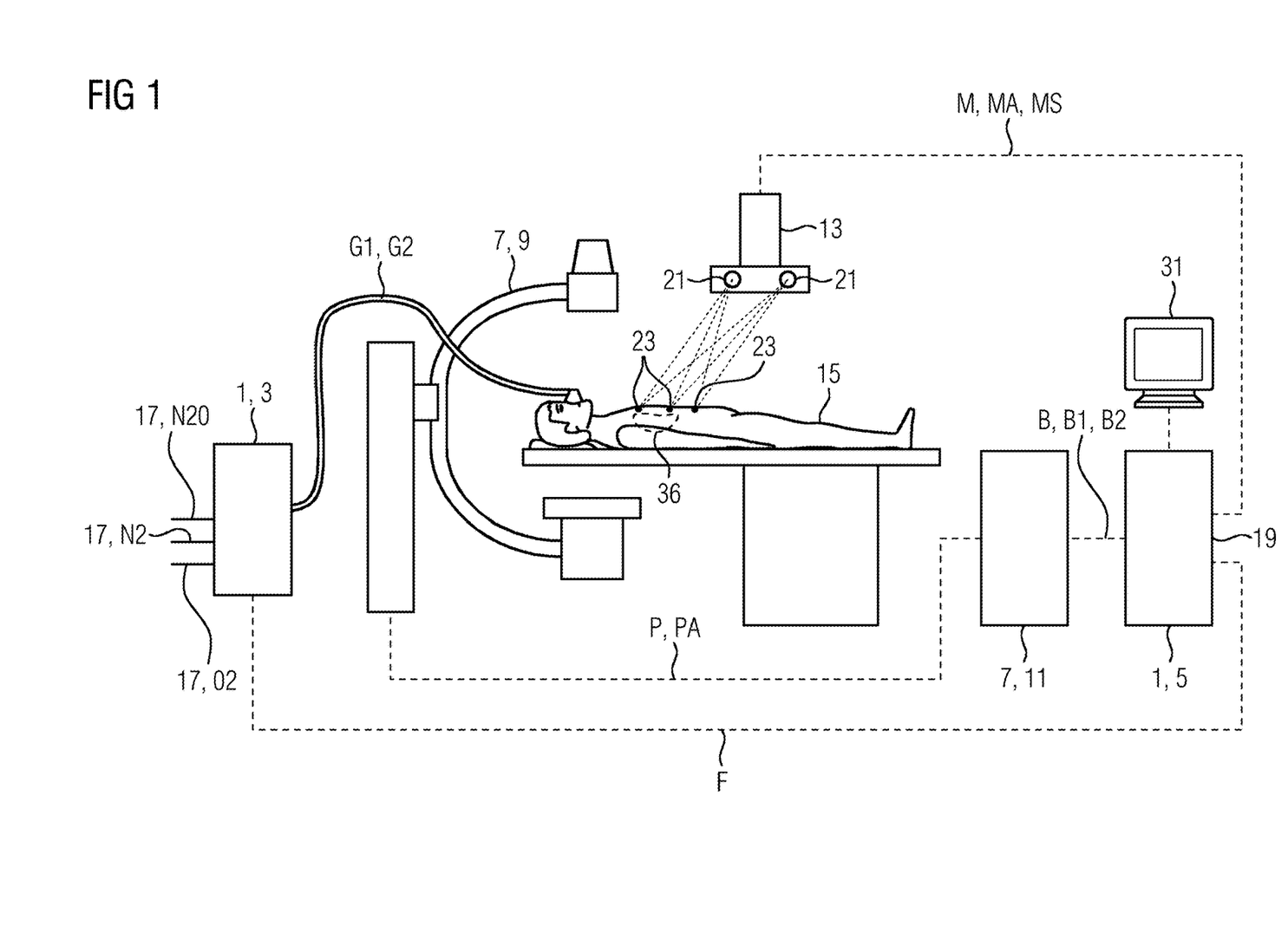
FIG. 1 depicts in a schematic block diagram anesthesia equipment with a ventilator for ventilating a patient and with a control unit; a medical imaging device in the form of an X-Ray C-arm system and an optical tracking system with which the anesthesia equipment interacts according to an embodiment.

FIG. 1 depicts in a schematic block diagram anesthesia equipment 1 with a ventilator 3 and a control unit 5. FIG. 1 also depicts a medical imaging device 7, that includes a (X-ray) C-arm 9 and an image computer 11. Optionally, an optical tracking system 13 is also present. The imaging device 7 and the tracking system 13 interact here with the anesthesia equipment 1 but do not themselves form an integral part of the latter.

In an embodiment, the ventilator 3 of the anesthesia equipment 1 is formed by a THRIVE ventilator that is conventional per se, that is configured to supply a patient 15 with a respiratory gas G1. For example, the patient 15 is supplied here with pure oxygen with a high flow rate F, unidirectionally and in a manner unmodulated over time, as the respiratory gas G1. The flow rate F may be adjusted here within a medically safe range, for example between 50 liters per minute and 90 liters per minute. The respiratory gas G1 is supplied to the patient 15 via the nose or alternatively via a ventilation tube (endotracheal tube). The supply of the respiratory gas G1, that is unmodulated over time, leads to motionless ventilation of the patient 15, in other words it does not cause any lasting movement of the patient's body.

In an embodiment, the ventilator 3, in addition to the THRIVE ventilator, includes conventional anesthesia equipment, that is configured to supply the patient 15 with a respiratory gas G2 with periodically alternating gas flow direction. Using this conventional anesthesia equipment, the ventilator 3 carries out conventional motion ventilation in which the gas flow direction of the respiratory gas G2 is slowly, with a frequency corresponding approximately to the natural respiratory rhythm, and actively alternated. The ventilator 3 generates a body movement corresponding to the customary respiratory movement of the patient 15 in which thorax and abdominal wall of the patient 15 periodically rise and fall and the internal organs in the chest area and abdominal region of the patient periodically change their position owing to the varying lung volume.

The respiratory gas G2 is a mixture of pure oxygen and nitrogen gas or purified ambient air with an oxygen content that substantially matches the customary oxygen content of air or is slightly raised compared thereto. Optionally, a proportion of the anesthetic, for example laughing gas (nitrous oxide, $N_2O$) is also added to the respiratory gas G2.

In order to produce the respiratory gases G1 and G2 the ventilator 3 includes connecting lines 17 for oxygen O2, nitrogen N2 or air and laughing gas N2O, that are fed from a supply network of a hospital and/or from corresponding gas bottles.

Optionally, the anesthesia equipment 1 also includes an injection device (not shown), that is configured to inject the patient 15 with a liquid anesthetic.

The C-arm 9 of the imaging device 7 is configured to acquire digital (X-ray) projection images P of the inside of the body of the patient 15 from different perspectives and to transfer them to the image computer 11. The image computer 11 is configured to calculate a digital (3D) image data set B of the inside of the body of the patient 15 from these projection images P using conventional image reconstruction algorithms.

The tracking system 13 includes a (3D) camera 21 with an electronic image processing device, that is configured to determine the position M in the three-dimensional space of a plurality of (adhesive) markings 23 provided on the body of the patient 15 from images acquired by the 3D camera 21.

The control unit 5 is formed, for example, by a computer (for example a personal computer). A control program 19 is installed to be executable in the control unit 5 and automatically carries out an anesthesia procedure described below. The projection images P and 3D image data sets B of the patient 15 as well as the positions M of the adhesive markings 23, if present, determined by the tracking system 13 are supplied as input variables to the control unit 5 by the image computer 11 of the imaging device 7.

The control unit 5 in turn actuates the ventilator 3 as well as, optionally, the imaging device 7.

Figure 2:
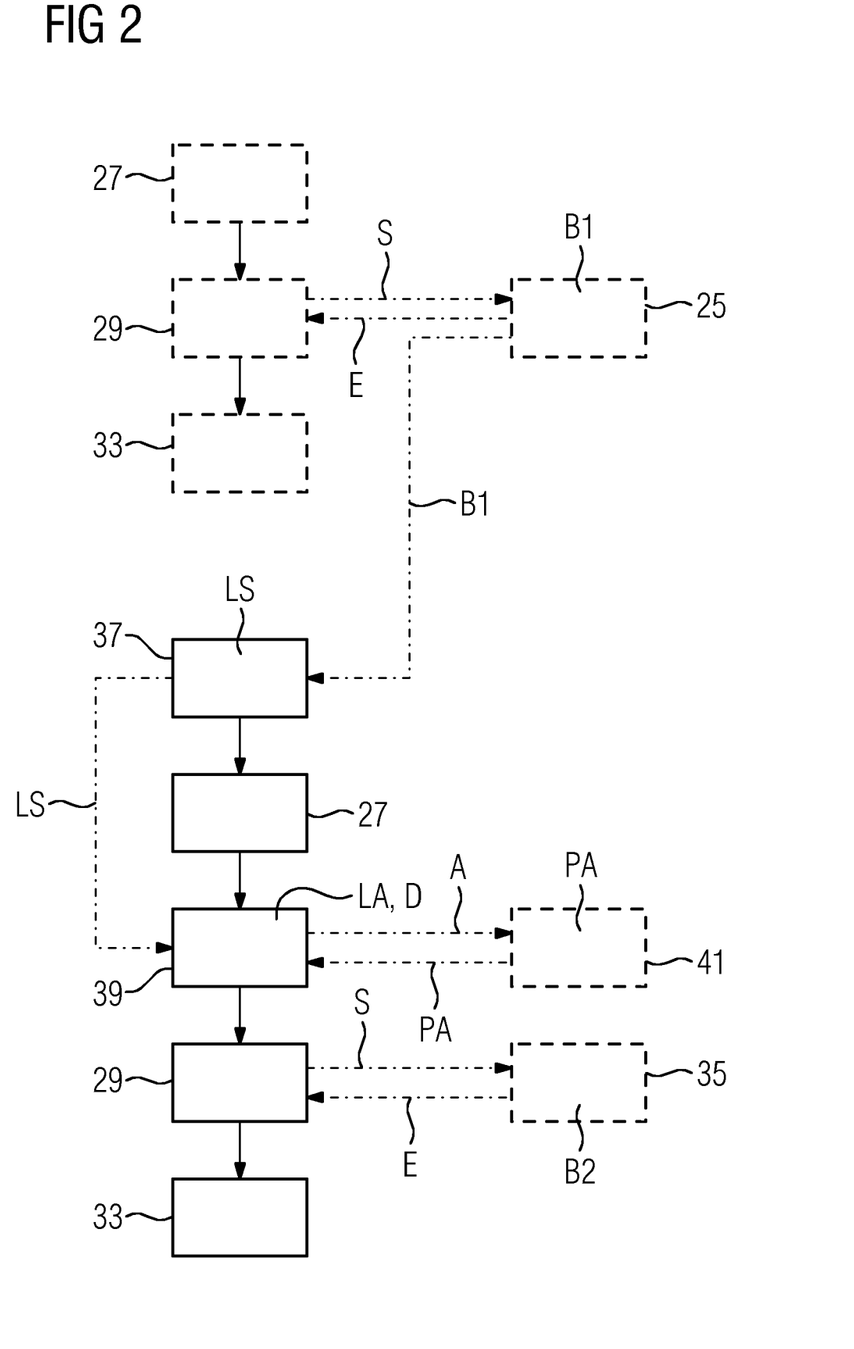
FIG. 2 depicts in a schematic simplified flow diagram an anesthesia procedure carried out by the anesthesia equipment according to FIG. 1 for ventilation of an anesthetized patient during acquisition of a medical 3D image data set according to an embodiment.

FIG. 2 schematically represents one embodiment of the anesthesia procedure carried out by the anesthesia equipment 1 in an application in which the anesthesia procedure for ventilation of the patient 15 is used during acquisition of a medical (3D) image data set B2 (generally also referred to as a "scan") of the inside of the body by the imaging device 7. This imaging acquisition is, for example, a follow-up scan, that is carried out as an interval of, for example, several days or weeks, after a first scan, in other words a first (3D) image data set B1 acquired in advance, in order, for example, to document the course of a disease or a therapy. To provide the comparability and/or simple ability to register the image data sets B1 and B2 it is regularly of great importance that the image data sets B1 and B2 map the inside of the body of the patient 15 at an interval that is a similar as possible, and this is complicated by the respiration-induced body movement of the patient 15.

Only the method steps, that are entered in the diagram according to FIG. 2 as rectangles denoted by solid lines, form part of the actual anesthesia procedure. Further measures, that do not form part of the anesthesia procedure but merely provide input data for this procedure or are carried out at the same time as the anesthesia procedure, are represented in FIG. 2 as rectangles denoted by dotted lines. Arrows denoted by solid lines identify a successive implementation of the method steps connected therewith. Arrows denoted by dot-dash lines represent a transfer of data and other signals.

In the application case according to FIG. 2, the image data set B1 is acquired, for example, by the imaging device 7, as a preparatory action before implementation of the anesthesia procedure. To avoid movement artifacts during image acquisition the image data set B1 is acquired optionally under anesthesia and deactivation of the respiratory movement of the patient 15. For this, the patient 15 is anesthetized in a step 27, for example by anesthesia equipment 1, and is motionlessly ventilated by THRIVE (as described above) with the respiratory gas G1 at a specified flow rate of, for example, 70 liters per minute.

As soon as the anesthetized test state is achieved, image acquisition (step 25) is automatically started or provided for manual implementation. In the first case, for example the control unit 5 of the anesthesia equipment 1 emits in a step 29 a start signal S to the imaging device 7, which thereupon automatically begins the image acquisition. In the second case, the control unit 5 outputs the start signal S, for example via a connected screen 31 (see FIG. 1), in order to signal enabling of image acquisition to a radiologist carrying out the treatment.

After the image data set B1 has been acquired, an end signal E is returned to the control unit 5—automatically by the imaging device 7 or manually by the radiologist—which thereupon cancels the anesthesia in a step 33.

During the course of the anesthesia procedure, that according to FIG. 2 is carried out in accompaniment to the follow-up scan, in other words the acquisition of the subsequent image data set B2 (step 35), the control unit 5 determines initially in a step 37 a desired location LS of a body part 36 (see FIG. 1) of the patient 15, for example a lobe of the lung, from the image data set B1 used here as the default image data set. For this, a 2-dimensional projection representation according to a specified characteristic perspective is derived, for example from the 3D image data set B1. The contour of the body part 36 is then determined in this projection representation using methods of automatic image recognition, for example segmentation. For example, the coordinates of the determined contour line, that for comparability are indicated relative to the stationary body structures, are used as the desired location LS.

The anesthesia is then (alternatively before or at the same time as step 37) initiated (step 27) by the anesthesia equipment 1 as described above.

In a subsequent step 39, the control unit 5 induces the imaging device 7 to acquire a current image data set of the inside of the body of the patient 15 (step 41) by emitting a request signal A once or several times. The current image data set is acquired, for example by the C-arm 9, as a two-dimensional projection image PA from the same perspective, that formed the basis of the creation of the projection representation in step 37 and determination of the desired location LS, therefore (step 41).

Analogously to step 37, the control unit 5 determines from the projection image PA the contour of the body part 36 (for example here the lobe of the lung, therefore) and determines a current location LA of the body part 36 hereby.

The control unit 5 changes an adjustment parameter of the ventilator 3, for example the flow rate F (FIG. 1) of the respiratory gas G1, on the basis of the difference D of the current location LA of the body part 36 from the desired location LS, so the current location LA is adjusted to the desired location LS. For example, the flow rate F is increased, so the lobe of the lung used as the body part 36 is inflated to a volume corresponding to the state in image data set B1.

Furthermore, the adjustment parameter F of the ventilator 3 may be controlled or regulated in such a way that the specified desired location LS is adjusted to a specified temporal desired path PS. The specified temporal desired path PS may include a plurality of desired locations LS, that may be achieved, for example in a chronological sequence, by an adjustment of the current location LA.

As soon as this adjustment has been made the control unit 5 outputs the start signal S (step 29) to start or provide the follow-up scan and therewith the acquisition of image data set B2 (step 35). On the end signal E, that announces completion of the follow-up scan, the control unit 5 then in turn ends the anesthesia (step 33).

Figure 3:
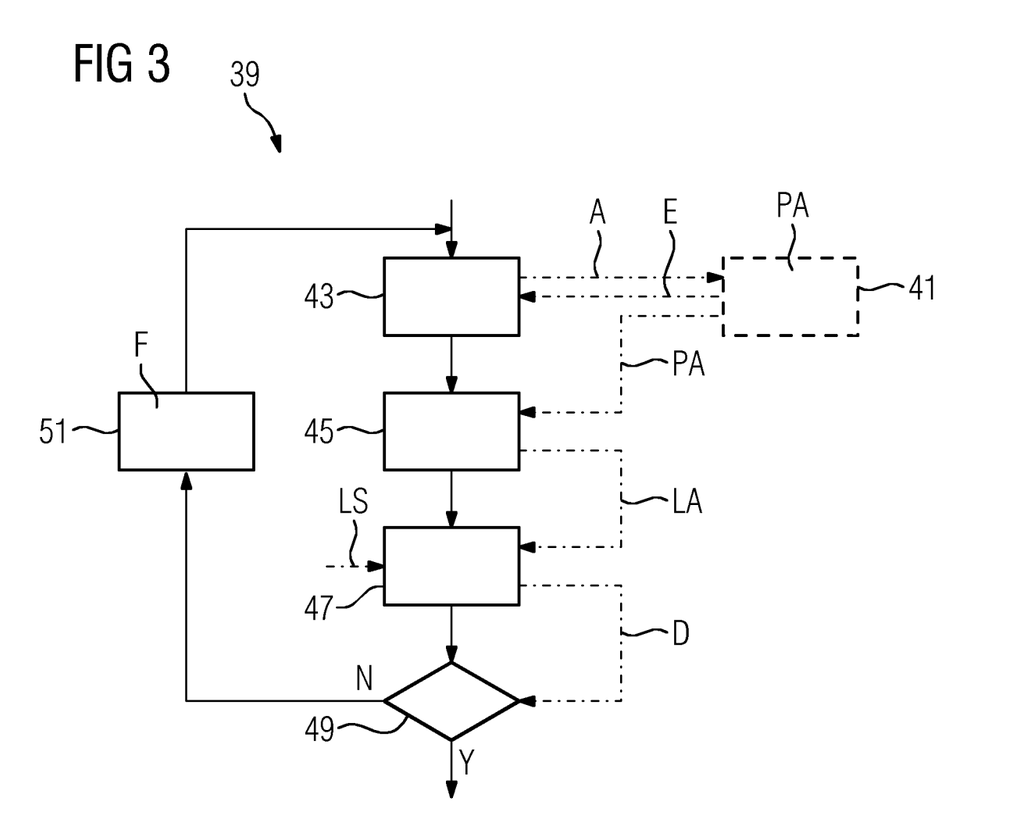
FIG. 3 depicts in more detail in a representation according to FIG. 2 a step of the method there in which an adjustment parameter of the ventilator is regulated in such a way that a current location of a body part of the patient is adjusted to a specified desired location according to an embodiment.

In step 39, described above in a very simplified manner, the control unit 5 carries out, in detail, an iterative closed-loop control shown in more detail in FIG. 3.

In a first step 43 of this closed-loop control, the control unit 5 induces the imaging device 7 to acquire the current projection image PA (step 41) by emitting the request signal A. On the end signal E (for example automatically generated by the imaging device 7), the control unit 5 determines in a step 45 the current location LA of the body part 36 by evaluation of the projection image PA (for example by automatic segmentation).

In a following step 47, the control unit 5 determines the difference D of the current location LA from the desired location LS. As a measure for the difference D the control unit 5 uses, for example, the size of the non-overlapping surface areas within the contour lines of the body part 36 extracted from the image data set B1 and the current projection image PA. The control unit 5 tests the difference D in a step 49 in respect of a specified termination criterion, for example for undershooting a specified tolerance limit. As soon as the termination criteria is met (Y), if the difference D undershoots the tolerance limit, therefore, the control unit 5 ends the closed-loop control.

Otherwise (N), in a step 51, the control unit 5, by appropriate actuation of the ventilator 3, induces the change in the flow rate F. The control unit 5 determines the size and direction of this change, for example according to the Newton method. The flow rate F is changed, for example, in such a way that, as a consequence of the changed flow rate F, the current location LA of the body part 36 approaches the desired location LS. The control unit 5 then jumps back to step 43 and runs through the closed-loop control again, therefore.

Figure 4:
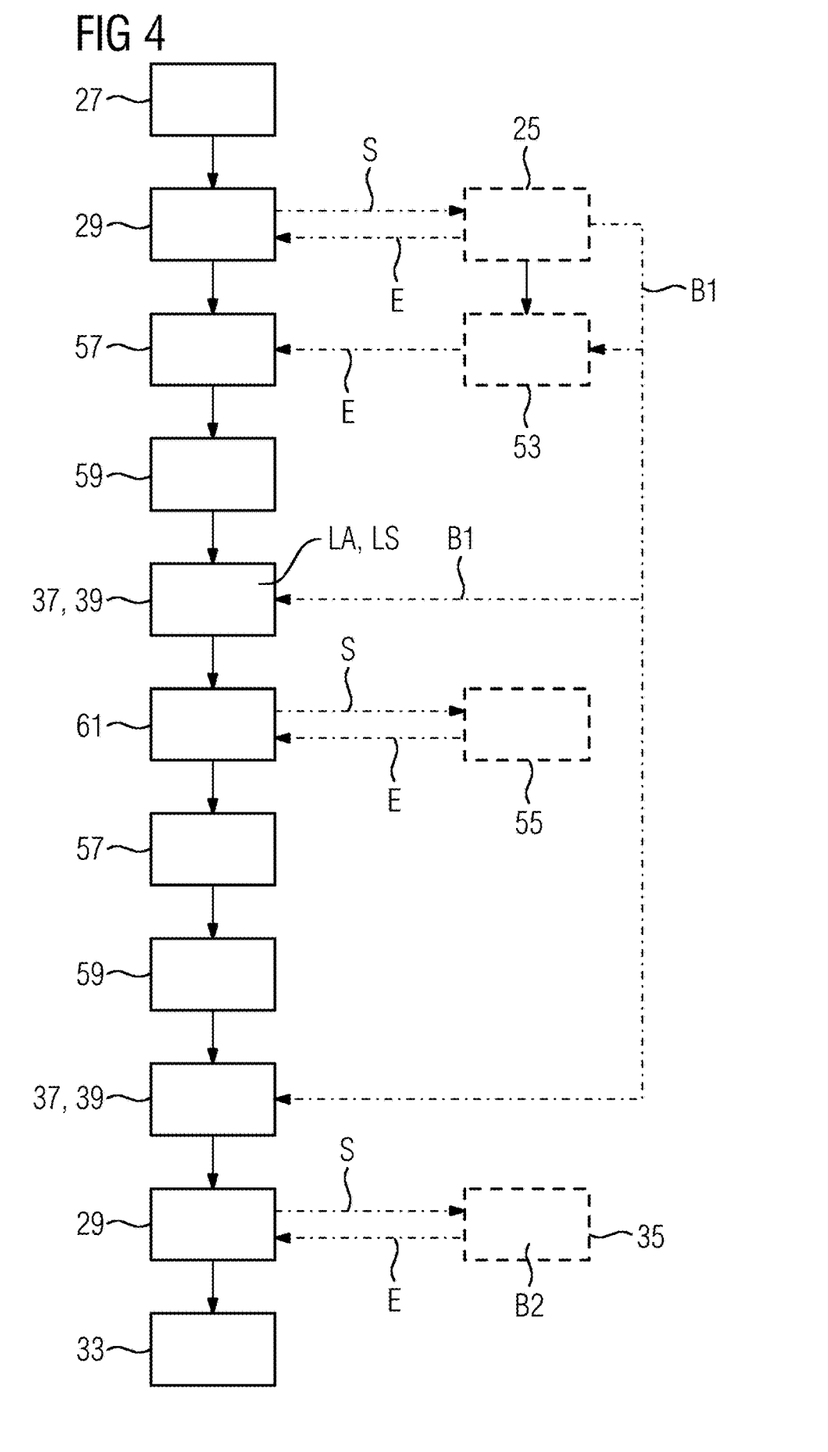
FIG. 4 depicts in a representation according to FIG. 2 a further application of the anesthesia procedure for ventilation of an anesthetized patient during an image-assisted intervention according to an embodiment.

FIG. 4 depicts another application case of the anesthesia procedure in which this is used for ventilation of the patient 15 during an image-assisted medical intervention.

Parallel to the anesthesia procedure, but not as part of it, firstly a first scan (step 25) is carried out. The image data set B1 resulting therefrom is used for treatment planning (step 53). The actual intervention (step 55), for example the introduction of a catheter into the upper body of the patient 15, is performed according to the treatment planning. In order to check the success of treatment a follow-up scan (step 35) is finally again performed.

An optimally uniform location of the organs and other body parts in the chest area and abdominal region of the patient 15 is in turn required for steps 25, 55 and 35. However, motionless ventilation of the patient 15 is often not possible for the entire duration of steps 25, 53, 55 and 35. During the course of the anesthesia procedure, the control unit 5 repeatedly switches the ventilator 3 back and forth between the operating modes of motionless ventilation (THRIVE) and conventional motion ventilation.

In detail, the anesthesia equipment 1 initially anaesthetizes the patient 15 (step 27) by motionless ventilation (THRIVE) and induces the first scan (step 25) in step 29.

Upon receiving the end signal E, the control unit 5 switches the ventilator 3 in a step 57 for the duration of the treatment planning (step 53) from motionless ventilation (THIRVE) to motion ventilation.

Completion of treatment planning is signaled to the control unit 5 by a (for example manually generated) further end signal E. Hereupon the control unit 5 switches over the ventilator 3 again in a step 59 from motion ventilation to motionless ventilation (THRIVE) and adjusts the current location LA of the body part 36 by carrying out steps 37 and 39 by regulation of the flow rate F to the desired location LS derived from the image data set B1.

In a step 61, the control unit 5 then provides implementation of the intervention (step 55) by emitting the start signal S once again.

After receiving the end signal E, that in this case indicates completion of the intervention, the control unit 5 switches over the ventilator 3 again from motionless ventilation (THRIVE) to motion ventilation (step 57), for example to reduce an elevated $CO_2$ concentration in the blood of the patient 15.

For implementation of the follow-up scan, control unit 5 switches over (step 59) the ventilator 3 again at a subsequent instant from motion ventilation to motionless ventilation (THRIVE), adjusts the current location LA of the body part 36 again by regulation of the flow rate F to the desired location LS derived from the image data set B1 (steps 37 and 39) and with renewed implementation of step 29 induces the follow-up scan, for example the acquisition of image data set 2 (step 35).

After completion of acquisition and reception of the corresponding end signal E the control unit 5 then in turn ends the anesthesia (step 33).

In an embodiment of the anesthesia procedure (not shown), the desired location LS of the body part 36 is not determined from a default image data set. Instead, the position M of the adhesive markings 23 on the body of the patient 15 is determined by the tracking system 13 here, for example at the instant of a first scan, as an indirect reference (desired position MS, see FIG. 1) for the desired location LS.

For regulated adjustment of the current location LA of the body part 36 to the desired location LS, for example analogous to step 39 in FIG. 2 before a follow-up scan, a current position MA (FIG. 1) of the adhesive markings 23 is determined during the anesthesia and motionless ventilation (THRIVE) of the patient 15 by the tracking system 13. For each adhesive marking 23, the control unit 5 determines the difference of the current position MA from the desired position MS and adjusts the adjustment parameter of the ventilator 3, for example the flow rate F, analogously to the closed-loop control in FIG. 3 in such a way that the current position MA of every adhesive marking 23 within specified tolerance limits is matched to the desired location MS. The current location LA of the body part 36 is also indirectly adjusted thereby to the desired location LS.

In a further embodiment of the anesthesia equipment 1, the ventilator 3, for example as an alternative to the THRIVE apparatus, includes a further ventilator for carrying out jet ventilation. During operation of this apparatus the respiratory gas G1 is applied to the patient 15 in pulses and at a high pulse frequency (compared to the customary respiratory cycle) into the airways that are open to the outside. In addition to the (gas) flow rate F, the pulse frequency of the gas pulses may also be set here within a medically safe range, for example between 0.5 Hz and 10 Hz. Optionally, the mean pressure of the respiratory gas G1, by which the instantaneous pressure of the respiratory gas G1 fluctuates as a consequence of the pulsed application, may be set in addition to the flow rate and/or the pulse frequency. A rapid movement with low amplitude—corresponding to the pulse frequency—is generated in the body of the patient 15 by the jet ventilation, which movement fundamentally differs from a customary respiratory movement of the body.

For example, air with a customary or slightly enriched oxygen content as well as the optional addition of at least one gaseous anesthetic is used as the respiratory gas G1 in this variant of the anesthesia equipment 1.

Within the framework of the anesthesia procedure, jet ventilation is used as the method of motionless ventilation instead of the THRIVE anesthesia used in the examples described above.

Figure 5:
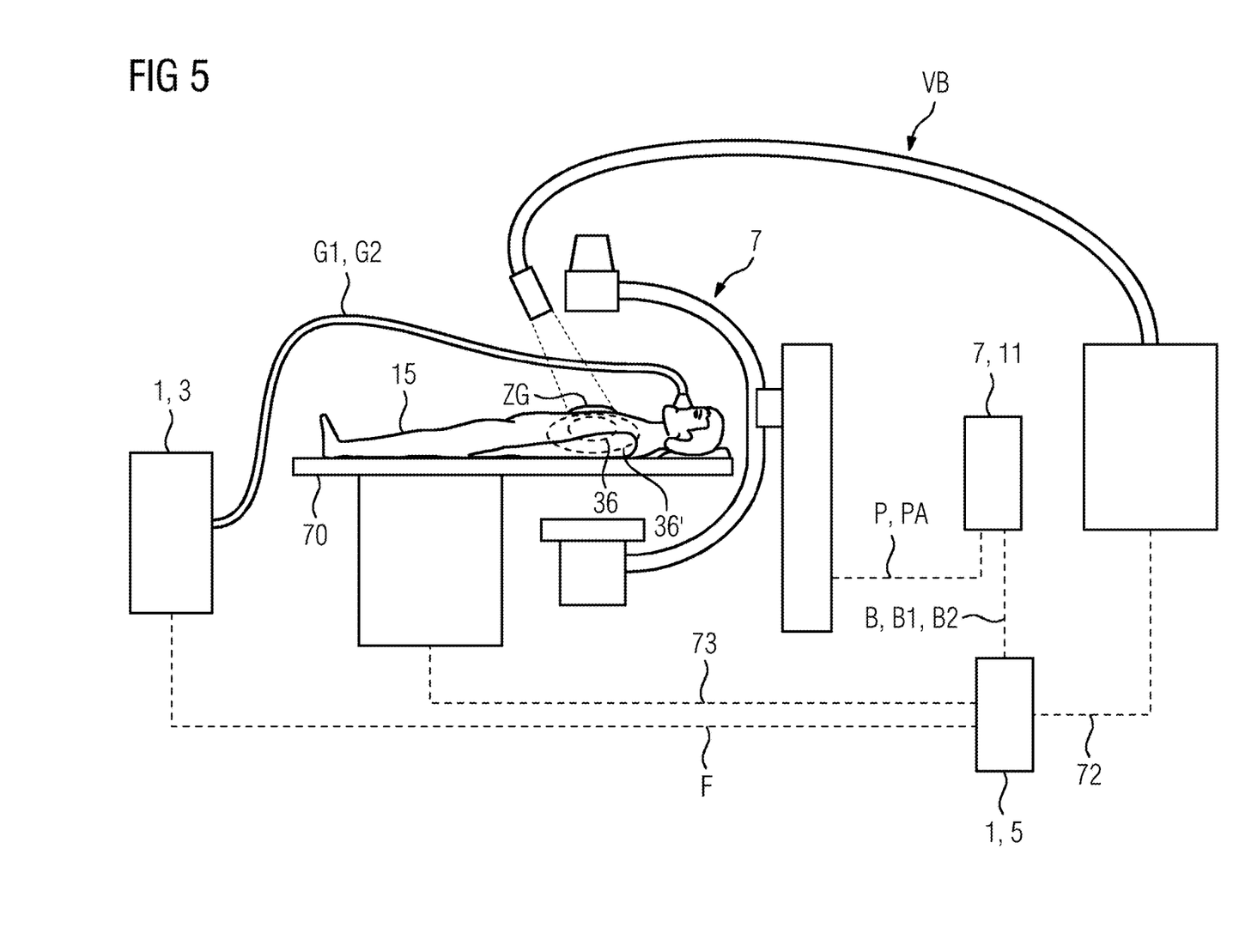
FIG. 5 depicts in a schematic block diagram anesthesia equipment with a ventilator for ventilation of a patient arranged on a patient supporting device, with a control unit and a movable device for irradiation according to an embodiment.

In a schematic block diagram FIG. 5 depicts anesthesia equipment 1 with a ventilator 3 for ventilating a patient 15 arranged on a patient supporting device 70, and a control unit 5. In the embodiment illustrated here, the desired location LS may be specified on the basis of a schedule of a device for irradiation VB. For this, the device for irradiation VB may include, for example, a control unit, that is configured to send a corresponding control command 72 to the control unit 5.

Furthermore, the device for irradiation VB may be moveable. Advantageously, a regulated adjustment of the desired location LS and a movement trajectory of the device for irradiation VB may take place hereby. Regulation by the control unit 5 by the specification of the adjustment parameter F and/or a control command 72 to the device for irradiation VB may be conducive for this.

Furthermore, a control parameter, for example an operating parameter of a movement and/or for control of an irradiation intensity, of the device for irradiation VB may be adjusted as a function of the current location LA. The schedule of the device for irradiation VB may include, for example, a spatial distribution of irradiation dose. An adjustment of the control parameter as a function of the current location LA ensures that the at least one body part 36 of the patient 15 may be irradiated in accordance with the specified schedule. Furthermore, it is possible to ensure that further body parts 36' of the patient 15 are always arranged outside of a target area ZG of the device for irradiation VB.

In an embodiment, the patient supporting device 70, on which the patient 15 is arranged, may be moveable. As a result, the adjustment of the location LA of the at least one body part 36 of the patient 15 to the specified desired location LS may take place at least partially by the movement of the patient supporting device 70. For this, the control unit 5 may send a control command 73 to the patient supporting device 70. The movement of the patient supporting device 17 may take place, for example, semi-automatically and/or automatically.

It is to be understood that the elements and features recited in the appended claims may be combined in different ways to produce new claims that likewise fall within the scope of the present embodiments. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present embodiments have been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. An anesthesia procedure comprising:
   supplying a patient whose own respiratory drive is suspended by a ventilator with a first respiratory gas with a unidirectional flow or a rapidly alternating flow direction with a frequency of between 0.5 and 10 Hertz; and
   controlling at least one adjustment parameter of the ventilator in such a way that a current location of at least one body part of the patient is adjusted to a specified desired location, wherein the at least one adjustment parameter of the ventilator is controlled in such a way that the specified desired location is adjusted to a specified temporal desired path that includes a plurality of locations in a chronological sequence.

2. The anesthesia procedure of claim 1, wherein the specified desired location is specified based on a schedule of a device for irradiation.

3. The anesthesia procedure of claim 2, wherein the device for irradiation is movable, wherein the anesthesia procedure further comprises:
   performing a regulated adjustment of the specified desired location; and
   moving the device for irradiation.

4. The anesthesia procedure of claim 2, further comprising:
adjusting a control parameter of the device for irradiation as a function of the current location.

5. The anesthesia procedure of claim 1, wherein the patient is arranged on a movable patient supporting device, wherein the current location of the at least one body part of the patient is adjusted to the specified desired location at least partially by a movement of the patient supporting device.

6. The anesthesia procedure of claim 1 wherein a flow rate, a pressure, an oxygen concentration, or a modulation of the flow rate or of the pressure of the first respiratory gas is controlled as the at least one adjustment parameter of the ventilator.

7. The anesthesia procedure of claim 1, wherein the specified desired location of the body part is determined based on a default image data set of the body of the patient.

8. The anesthesia procedure of claim 7, further comprising:
generating a current image data set of the body of the patient;
determining the current location of the body part based on the current image data set; and
changing the at least one adjustment parameter of the ventilator in such a way that the current location of the body part approaches the specified desired location.

9. The anesthesia procedure of claim 1, wherein the specified desired location of the body part is determined indirectly based on a desired position of at least one marking provided in or on the patient.

10. The anesthesia procedure of claim 9, further comprising: determining a current position of the at least one marking; and wherein the at least one adjustment parameter of the ventilator is changed in such a way that the current position of the at least one marking approaches its desired position.

11. The anesthesia procedure of claim 1, further comprising: starting, following adjustment of the current location of the body part to the specified desired location, image acquisition of the body of the patient.

12. The anesthesia procedure of claim 11, wherein at an end of or during an interruption to the image acquisition of the patient, ventilation is continued with a second respiratory gas with a slowly alternating flow direction with a frequency below or equal to 0.5 Hertz.

13. A system comprising:
a ventilator, which in a first operating mode is configured to supply a patient, whose own respiratory drive is suspended, with a first respiratory gas with unidirectional flow or rapidly alternating flow direction with a frequency of between 0.5 and 10 Hertz; and
a control unit that is configured to control or regulate at least one adjustment parameter of the ventilator to adjust a current location of at least one body part of the patient to a desired location, wherein the at least one adjustment parameter of the ventilator is controlled in such a way that the specified desired location is adjusted to a specified temporal desired path that includes a plurality of locations in a chronological sequence.

14. The system of claim 13, wherein the control unit is configured to specify the desired location based on a schedule of a device for irradiation.

15. The system of claim 14, wherein the control unit, on irradiation of the at least one body part of the patient by a movable device for irradiation, is configured to perform a regulated adjustment of the specified temporal desired path and of a movement trajectory of the device for irradiation.

16. The system of claim 15, wherein the control unit is configured to adjust a control parameter of the movable device for irradiation during an irradiation of the at least one body part of the patient, as a function of the current location.

17. The system of claim 13, wherein the control unit is configured to adjust the current location of the at least one body part of the patient, who is arranged on a moveable patient supporting device, to the desired location at least partially by a movement of the patient supporting device.

18. The system of claim 13, wherein the control unit is configured to control or regulate at least one of a flow rate, a pressure, an oxygen concentration, or a modulation of the flow rate or of the pressure of the first respiratory gas as the at least one adjustment parameter of the ventilator.

19. The system of claim 13, wherein the control unit is configured to determine the desired location of the body part based on a default image data set of the body of the patient.

20. The system of claim 13, wherein the control unit is configured to determine the desired location of the body part based on a desired position, detected by a tracking mechanism, of at least one marking provided in or on the patient.

21. The system of claim 13, wherein the control unit, following adjustment of the current location of the body part to the desired location, is configured to start or enable image acquisition of the body of the patient or an intervention inside the body of the patient.

22. The system of claim 21, wherein the ventilator, in a second operating mode, is configured to supply the patient with a second respiratory gas with a slowly alternating flow direction with a frequency below or equal to 0.5 Hertz, wherein the control unit is configured to switch over the ventilator from the first operating mode into the second operating mode at an end of or during an interruption to the image acquisition or the intervention.

\* \* \* \* \*